United States Patent
Vasquez et al.

(10) Patent No.: US 6,329,511 B1
(45) Date of Patent: Dec. 11, 2001

(54) HUMANIZED ANTIBODIES TO γ-INTERFERON

(75) Inventors: Maximiliano Vasquez, Palo Alto; Nicholas F. Landolfi, Menlo Park; Naoya Tsurushita, Palo Alto; Cary L. Queen, Los Altos, all of CA (US)

(73) Assignee: Protein Design Labs, Inc., Fremont, CA (US)

( * ) Notice: Subject to any disclaimer, the term of this patent is extended or adjusted under 35 U.S.C. 154(b) by 0 days.

(21) Appl. No.: 09/450,520

(22) Filed: Nov. 29, 1999

Related U.S. Application Data

(60) Provisional application No. 60/110,523, filed on Dec. 1, 1998.

(51) Int. Cl.[7] .............................. C07K 16/00; C12P 21/08
(52) U.S. Cl. ................................. 530/388.23; 530/387.1; 530/387.3
(58) Field of Search ........................... 530/387.1, 388.23, 530/387.3

(56) References Cited

U.S. PATENT DOCUMENTS

| | | |
|---|---|---|
| 5,530,101 | 6/1996 | Queen et al. . |
| 5,585,089 | 12/1996 | Queen et al. . |
| 5,693,761 | 12/1997 | Queen et al. . |
| 5,693,762 | 12/1997 | Queen et al. . |

OTHER PUBLICATIONS

Colman, PM Res. Immunology 145:33–36, 1994.*

\* cited by examiner

*Primary Examiner*—Patrick J. Nolan
*Assistant Examiner*—Gerald R. Ewoldt
(74) *Attorney, Agent, or Firm*—Townsend and Townsend and Crew LLP

(57) ABSTRACT

The invention provides humanized immunoglobulins that bind to and neutralize γ-interferon. The antibodies are useful for treatment of diseases of the immune system, particularly autoimmune diseases.

8 Claims, 4 Drawing Sheets

ATGGAATCACAGACTCTGGTCTTCATATCCATACTGCTCTGGTTATATGGTGCTGATGGG
 M  E  S  Q  T  L  V  F  I  S  I  L  L  W  L  Y  G  A  D  G

AACATTGTTATGACCCAATCTCCCAAATCCATGTACGTGTCAATAGGAGAGAGGGTCACC
 N  I  V  M  T  Q  S  P  K  S  M  Y  V  S  I  G  E  R  V  T

TTGAGCTGCAAGGCCAGTGAAAATGTGGATACTTATGTATCCTGGTATCAACAGAAACCA
 L  S  C  K  A  S  E  N  V  D  T  Y  V  S  W  Y  Q  Q  K  P

GAGCAGTCTCCTAAACTGCTGATATATGGGGCATCCAACCGGTACACTGGGGTCCCCGAT
 E  Q  S  P  K  L  L  I  Y  G  A  S  N  R  Y  T  G  V  P  D

CGCTTCACGGGCAGTGGATCTGCAACAGATTTCACTCTGACCATCAGCAGTGTGCAGGCT
 R  F  T  G  S  G  S  A  T  D  F  T  L  T  I  S  S  V  Q  A

GAAGACCTTGCAGATTATCACTGTGGACAGAGTTACAACTATCCATTCACGTTCGGCTCG
 E  D  L  A  D  Y  H  C  G  Q  S  Y  N  Y  P  F  T  F  G  S

GGGACAAAGTTGGAAATAAAG
 G  T  K  L  E  I  K

FIG. 1A

ATGGGATGGAGCTGTATCATCCTCTTCTTGGTAGCAACAGCTACAGGTGTCCTCTCCCAG
 M  G  W  S  C  I  I  L  F  L  V  A  T  A  T  G  V  L  S  Q

GTCCAACTGCAGCAGCCTGGGGCTGACCTTGTGATGCCTGGGGCTCCAGTGAAGCTGTCC
 V  Q  L  Q  Q  P  G  A  D  L  V  M  P  G  A  P  V  K  L  S

TGCTTGGCTTCTGGCTACATCTTCACCAGCTCCTGGATAAACTGGGTGAAGCAGAGGCCT
 C  L  A  S  G  Y  I  F  T  S  S  W  I  N  W  V  K  Q  R  P

GGACGAGGCCTCGAGTGGATTGGAAGGATTGATCCTTCCGATGGTGAAGTTCACTACAAT
 G  R  G  L  E  W  I  G  R  I  D  P  S  D  G  E  V  H  Y  N

CAAGATTTCAAGGACAAGGCCACACTGACTGTAGACAAATCCTCCAGCACAGCCTACATC
 Q  D  F  K  D  K  A  T  L  T  V  D  K  S  S  S  T  A  Y  I

CAACTCAACAGCCTGACATCTGAGGACTCTGCGGTCTATTACTGTGCTAGAGGATTTCTG
 Q  L  N  S  L  T  S  E  D  S  A  V  Y  Y  C  A  R  G  F  L

CCCTGGTTTGCTGACTGGGGCCAAGGGACTCTGGTCACTGTCTCTGCA
 P  W  F  A  D  W  G  Q  G  T  L  V  T  V  S  A

FIG. 1B

```
ATGGAGACCGATACCCTCCTGCTATGGGTCCTCCTGCTATGGGTCCCAGGATCAACCGGA
 M  E  T  D  T  L  L  W  V  L  L  W  V  P  G  S  T  G

GATATTCAGATGACCCAGTCTCCGTCGACCCTCTCTGCTAGCGTCGGGGATAGGGTCACC
 D  I  Q  M  T  Q  S  P  S  T  L  S  A  S  V  G  D  R  V  T

ATAACCTGCAAGGCCAGTGAAAATGTGGATACTTATGTATCCTGGTATCAGCAGAAGCCA
 I  T  C  K  A  S  E  N  V  D  T  Y  V  S  W  Y  Q  Q  K  P

GGCAAAGCTCCCAAGCTTCTAATTTATGGGGCATCCAACCGGTACACTGGGGTACCTTCA
 G  K  A  P  K  L  L  I  Y  G  A  S  N  R  Y  T  G  V  P  S

CGCTTCAGTGGCAGTGGATCTGGGACCGATTTCACCCTCACAATCAGCTCTCTGCAGCCA
 R  F  S  G  S  G  S  G  T  D  F  T  L  T  I  S  S  L  Q  P

GATGATTTCGCCACTTATTACTGCGGACAGAGTTACAACTATCCATTCACGTTCGGTCAG
 D  D  F  A  T  Y  Y  C  G  Q  S  Y  N  Y  P  F  T  F  G  Q

GGGACCAAGGTGGAGGTCAAACGT
 G  T  K  V  E  V  K  R
```

*FIG. 2A*

```
ATGGGATGGAGCTGGATCTTTCTCTTCCTCCTGTCAGGTACCGCGGGCGTGCACTCTCAG
 M  G  W  S  W  I  F  L  F  L  L  S  G  T  A  G  V  H  S  Q

GTCCAGCTTGTCCAGTCTGGGGCTGAACTCAAGAAACCTGGGAGCTCCGTGAAGGTCTCC
 V  Q  L  V  Q  S  G  A  E  L  K  K  P  G  S  S  V  K  V  S

TGCAAAGCTTCTGGCTACATCTTTACTAGCTCCTGGATAAACTGGGTAAAGCAGGCCCCT
 C  K  A  S  G  Y  I  F  T  S  S  W  I  N  W  V  K  Q  A  P

GGACAGGGTCTCGAGTGGATTGGAAGGATTGATCCTTCCGATGGTGAAGTTCACTACAAT
 G  Q  G  L  E  W  I  G  R  I  D  P  S  D  G  E  V  H  Y  N

CAAGATTTCAAGGACAAGGCTACACTTACAGTCGACAAATCCACCAATACAGCCTACATG
 Q  D  F  K  D  K  A  T  L  T  V  D  K  S  T  N  T  A  Y  M

GAACTGAGCAGCCTGAGATCAGAGGACACTGCAGTCTATTACTGTGCAAGAGGATTTCTG
 E  L  S  S  L  R  S  E  D  T  A  V  Y  Y  C  A  R  G  F  L

CCCTGGTTTGCTGACTGGGGCCAAGGAACCCTGGTCACAGTCTCCTCAG
 P  W  F  A  D  W  G  Q  G  T  L  V  T  V  S  S
```

*FIG. 2B*

```
        1                                           31      36
huXAF   QVQLVQSGAELKKPGSSVKVSCKASGYIFT sswin WVRQAPGQGLEWIG
huZAF   QVQLVQSGAELKKPGSSVKVSCKASGYIFT sswin WVKQAPGQGLEWIG
DIFF    ------------*----------------- ----- --*----------
haf25   QVQLVQSGAEVKKPGSSVKVSCKASGYIFT sswin WVRQAPGQGLEWIG
DIFF    ---------*-------------------- ----- -*-----------

50                                        67                                          99
huXAF   ridpsdgevhymqdfkd KATLTVDKSTNTAYMELSSLRSEDTAVYYCAR gflpwfad WGQGTLVT
huZAF   ridpsdgevhymqdfkd KATLTVDKSTNTAYMELSSLRSEDTAVYYCAR gflpwfad WGQGTLVT
DIFF    ----------------- -------------------------------- -------- --------
haf25   ridpsdgevhymqdfkd KATLTVDKSTNTAYMELSSLRSEDTAVYYCAR gflpwfad WGQGTLVT
DIFF    XXXXXXXXXXXXXXXXX **-*-*-*-*---------------------- -------- --------
                                                                              107
                                                                   XXXXXXXX
```

FIG. 3

SEQUENCE LISTING

<160> NUMBER OF SEQ ID NOS: 13

<210> SEQ ID NO 1
<211> LENGTH: 381
<212> TYPE: DNA
<213> ORGANISM: Mus sp.
<220> FEATURE:
<221> NAME/KEY: CDS
<222> LOCATION: (1)..(381)
<223> OTHER INFORMATION: AF2 VL

<400> SEQUENCE: 1

```
atg gaa tca cag act ctg gtc ttc ata tcc ata ctg ctc tgg tta tat      48
Met Glu Ser Gln Thr Leu Val Phe Ile Ser Ile Leu Leu Trp Leu Tyr
 1               5                  10                  15 ggt gct gat ggg aac att gtt atg acc caa tct ccc aaa tcc atg tac      96
Gly Ala Asp Gly Asn Ile Val Met Thr Gln Ser Pro Lys Ser Met Tyr
             20                  25                  30 gtg tca ata gga gag agg gtc acc ttg agc tgc aag gcc agt gaa aat     144
Val Ser Ile Gly Glu Arg Val Thr Leu Ser Cys Lys Ala Ser Glu Asn
         35                  40                  45 gtg gat act tat gta tcc tgg tat caa cag aaa cca gag cag tct cct     192
Val Asp Thr Tyr Val Ser Trp Tyr Gln Gln Lys Pro Glu Gln Ser Pro
     50                  55                  60 aaa ctg ctg ata tat ggg gca tcc aac cgg tac act ggg gtc ccc gat     240
Lys Leu Leu Ile Tyr Gly Ala Ser Asn Arg Tyr Thr Gly Val Pro Asp
 65                  70                  75                  80 cgc ttc acg ggc agt gga tct gca aca gat ttc act ctg acc atc agc     288
Arg Phe Thr Gly Ser Gly Ser Ala Thr Asp Phe Thr Leu Thr Ile Ser
                 85                  90                  95 agt gtg cag gct gaa gac ctt gca gat tat cac tgt gga cag agt tac     336
Ser Val Gln Ala Glu Asp Leu Ala Asp Tyr His Cys Gly Gln Ser Tyr
            100                 105                 110 aac tat cca ttc acg ttc ggc tcg ggg aca aag ttg gaa ata aag         381
Asn Tyr Pro Phe Thr Phe Gly Ser Gly Thr Lys Leu Glu Ile Lys
        115                 120                 125
```

<210> SEQ ID NO 2
<211> LENGTH: 127
<212> TYPE: PRT
<213> ORGANISM: Mus sp.
<220> FEATURE:
<223> OTHER INFORMATION: AF2 VL

<400> SEQUENCE: 2

```
Met Glu Ser Gln Thr Leu Val Phe Ile Ser Ile Leu Leu Trp Leu Tyr
 1               5                  10                  15

Gly Ala Asp Gly Asn Ile Val Met Thr Gln Ser Pro Lys Ser Met Tyr
             20                  25                  30

Val Ser Ile Gly Glu Arg Val Thr Leu Ser Cys Lys Ala Ser Glu Asn
         35                  40                  45
```

```
Val Asp Thr Tyr Val Ser Trp Tyr Gln Gln Lys Pro Glu Gln Ser Pro
         50                  55                  60

Lys Leu Leu Ile Tyr Gly Ala Ser Asn Arg Tyr Thr Gly Val Pro Asp
 65                  70                  75                  80

Arg Phe Thr Gly Ser Gly Ser Ala Thr Asp Phe Thr Leu Thr Ile Ser
                 85                  90                  95

Ser Val Gln Ala Glu Asp Leu Ala Asp Tyr His Cys Gly Gln Ser Tyr
            100                 105                 110

Asn Tyr Pro Phe Thr Phe Gly Ser Gly Thr Lys Leu Glu Ile Lys
        115                 120                 125

<210> SEQ ID NO 3
<211> LENGTH: 408
<212> TYPE: DNA
<213> ORGANISM: Mus sp.
<220> FEATURE:
<221> NAME/KEY: CDS
<222> LOCATION: (1)..(408)
<223> OTHER INFORMATION: Description of Artificial Sequence:AF2 VH

<400> SEQUENCE: 3 atg gga tgg agc tgt atc atc ctc ttc ttg gta gca aca gct aca ggt      48
Met Gly Trp Ser Cys Ile Ile Leu Phe Leu Val Ala Thr Ala Thr Gly
 1               5                  10                  15 gtc ctc tcc cag gtc caa ctg cag cag cct ggg gct gac ctt gtg atg      96
Val Leu Ser Gln Val Gln Leu Gln Gln Pro Gly Ala Asp Leu Val Met
             20                  25                  30 cct ggg gct cca gtg aag ctg tcc tgc ttg gct tct ggc tac atc ttc     144
Pro Gly Ala Pro Val Lys Leu Ser Cys Leu Ala Ser Gly Tyr Ile Phe
         35                  40                  45 acc agc tcc tgg ata aac tgg gtg aag cag agg cct gga cga ggc ctc     192
Thr Ser Ser Trp Ile Asn Trp Val Lys Gln Arg Pro Gly Arg Gly Leu
     50                  55                  60 gag tgg att gga agg att gat cct tcc gat ggt gaa gtt cac tac aat     240
Glu Trp Ile Gly Arg Ile Asp Pro Ser Asp Gly Glu Val His Tyr Asn
 65                  70                  75                  80 caa gat ttc aag gac aag gcc aca ctg act gta gac aaa tcc tcc agc     288
Gln Asp Phe Lys Asp Lys Ala Thr Leu Thr Val Asp Lys Ser Ser Ser
                 85                  90                  95 aca gcc tac atc caa ctc aac agc ctg aca tct gag gac tct gcg gtc     336
Thr Ala Tyr Ile Gln Leu Asn Ser Leu Thr Ser Glu Asp Ser Ala Val
            100                 105                 110 tat tac tgt gct aga gga ttt ctg ccc tgg ttt gct gac tgg ggc caa     384
Tyr Tyr Cys Ala Arg Gly Phe Leu Pro Trp Phe Ala Asp Trp Gly Gln
        115                 120                 125 ggg act ctg gtc act gtc tct gca                                     408
Gly Thr Leu Val Thr Val Ser Ala
130                 135

<210> SEQ ID NO 4
<211> LENGTH: 136
<212> TYPE: PRT
<213> ORGANISM: Mus sp.
<220> FEATURE:
<223> OTHER INFORMATION: AF2 VH

<400> SEQUENCE: 4

Met Gly Trp Ser Cys Ile Ile Leu Phe Leu Val Ala Thr Ala Thr Gly
 1               5                  10                  15

Val Leu Ser Gln Val Gln Leu Gln Gln Pro Gly Ala Asp Leu Val Met
             20                  25                  30
```

```
Pro Gly Ala Pro Val Lys Leu Ser Cys Leu Ala Ser Gly Tyr Ile Phe
        35                  40                  45

Thr Ser Ser Trp Ile Asn Trp Val Lys Gln Arg Pro Gly Arg Gly Leu
    50                  55                  60

Glu Trp Ile Gly Arg Ile Asp Pro Ser Asp Gly Glu Val His Tyr Asn
 65                  70                  75                  80

Gln Asp Phe Lys Asp Lys Ala Thr Leu Thr Val Asp Lys Ser Ser Ser
            85                  90                  95

Thr Ala Tyr Ile Gln Leu Asn Ser Leu Thr Ser Glu Asp Ser Ala Val
            100                 105                 110

Tyr Tyr Cys Ala Arg Gly Phe Leu Pro Trp Phe Ala Asp Trp Gly Gln
        115                 120                 125

Gly Thr Leu Val Thr Val Ser Ala
        130                 135

<210> SEQ ID NO 5
<211> LENGTH: 384
<212> TYPE: DNA
<213> ORGANISM: Artificial Sequence
<220> FEATURE:
<223> OTHER INFORMATION: Description of Artificial Sequence:human-mouse
      transgenic construct HuZAF VL
<221> NAME/KEY: CDS
<222> LOCATION: (1)..(384)

<400> SEQUENCE: 5 atg gag acc gat acc ctc ctg cta tgg gtc ctc ctg cta tgg gtc cca     48
Met Glu Thr Asp Thr Leu Leu Leu Trp Val Leu Leu Leu Trp Val Pro
 1               5                  10                  15 gga tca acc gga gat att cag atg acc cag tct ccg tcg acc ctc tct     96
Gly Ser Thr Gly Asp Ile Gln Met Thr Gln Ser Pro Ser Thr Leu Ser
            20                  25                  30 gct agc gtc ggg gat agg gtc acc ata acc tgc aag gcc agt gaa aat    144
Ala Ser Val Gly Asp Arg Val Thr Ile Thr Cys Lys Ala Ser Glu Asn
        35                  40                  45 gtg gat act tat gta tcc tgg tat cag cag aag cca ggc aaa gct ccc    192
Val Asp Thr Tyr Val Ser Trp Tyr Gln Gln Lys Pro Gly Lys Ala Pro
    50                  55                  60 aag ctt cta att tat ggg gca tcc aac cgg tac act ggg gta cct tca    240
Lys Leu Leu Ile Tyr Gly Ala Ser Asn Arg Tyr Thr Gly Val Pro Ser
 65                  70                  75                  80 cgc ttc agt ggc agt gga tct ggg acc gat ttc acc ctc aca atc agc    288
Arg Phe Ser Gly Ser Gly Ser Gly Thr Asp Phe Thr Leu Thr Ile Ser
            85                  90                  95 tct ctg cag cca gat gat ttc gcc act tat tac tgc gga cag agt tac    336
Ser Leu Gln Pro Asp Asp Phe Ala Thr Tyr Tyr Cys Gly Gln Ser Tyr
            100                 105                 110 aac tat cca ttc acg ttc ggt cag ggg acc aag gtg gag gtc aaa cgt    384
Asn Tyr Pro Phe Thr Phe Gly Gln Gly Thr Lys Val Glu Val Lys Arg
        115                 120                 125

<210> SEQ ID NO 6
<211> LENGTH: 128
<212> TYPE: PRT
<213> ORGANISM: Artificial Sequence
<220> FEATURE:
<223> OTHER INFORMATION: Description of Artificial Sequence:human-mouse
      transgenic construct HuZAF VL

<400> SEQUENCE: 6

Met Glu Thr Asp Thr Leu Leu Leu Trp Val Leu Leu Leu Trp Val Pro
 1               5                  10                  15
```

```
Gly Ser Thr Gly Asp Ile Gln Met Thr Gln Ser Pro Ser Thr Leu Ser
            20                  25                  30

Ala Ser Val Gly Asp Arg Val Thr Ile Thr Cys Lys Ala Ser Glu Asn
        35                  40                  45

Val Asp Thr Tyr Val Ser Trp Tyr Gln Gln Lys Pro Gly Lys Ala Pro
    50                  55                  60

Lys Leu Leu Ile Tyr Gly Ala Ser Asn Arg Tyr Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Asp Asp Phe Ala Thr Tyr Tyr Cys Gly Gln Ser Tyr
            100                 105                 110

Asn Tyr Pro Phe Thr Phe Gly Gln Gly Thr Lys Val Glu Val Lys Arg
            115                 120                 125
```

<210> SEQ ID NO 7
<211> LENGTH: 409
<212> TYPE: DNA
<213> ORGANISM: Artificial Sequence
<220> FEATURE:
<223> OTHER INFORMATION: Description of Artificial Sequence:human-mouse
      transgenic construct HuZAF VH
<221> NAME/KEY: CDS
<222> LOCATION: (1)..(408)

<400> SEQUENCE: 7

```
atg gga tgg agc tgg atc ttt ctc ttc ctc ctg tca ggt acc gcg ggc      48
Met Gly Trp Ser Trp Ile Phe Leu Phe Leu Leu Ser Gly Thr Ala Gly
 1               5                  10                  15 gtg cac tct cag gtc cag ctt gtc cag tct ggg gct gaa ctc aag aaa      96
Val His Ser Gln Val Gln Leu Val Gln Ser Gly Ala Glu Leu Lys Lys
                20                  25                  30 cct ggg agc tcc gtg aag gtc tcc tgc aaa gct tct ggc tac atc ttt     144
Pro Gly Ser Ser Val Lys Val Ser Cys Lys Ala Ser Gly Tyr Ile Phe
            35                  40                  45 act agc tcc tgg ata aac tgg gta aag cag gcc cct gga cag ggt ctc     192
Thr Ser Ser Trp Ile Asn Trp Val Lys Gln Ala Pro Gly Gln Gly Leu
        50                  55                  60 gag tgg att gga agg att gat cct tcc gat ggt gaa gtt cac tac aat     240
Glu Trp Ile Gly Arg Ile Asp Pro Ser Asp Gly Glu Val His Tyr Asn
65                  70                  75                  80 caa gat ttc aag gac aag gct aca ctt aca gtc gac aaa tcc acc aat     288
Gln Asp Phe Lys Asp Lys Ala Thr Leu Thr Val Asp Lys Ser Thr Asn
                85                  90                  95 aca gcc tac atg gaa ctg agc agc ctg aga tca gag gac act gca gtc     336
Thr Ala Tyr Met Glu Leu Ser Ser Leu Arg Ser Glu Asp Thr Ala Val
            100                 105                 110 tat tac tgt gca aga gga ttt ctg ccc tgg ttt gct gac tgg ggc caa     384
Tyr Tyr Cys Ala Arg Gly Phe Leu Pro Trp Phe Ala Asp Trp Gly Gln
        115                 120                 125 gga acc ctg gtc aca gtc tcc tca g                                   409
Gly Thr Leu Val Thr Val Ser Ser
    130                 135
```

<210> SEQ ID NO 8
<211> LENGTH: 136
<212> TYPE: PRT
<213> ORGANISM: Artificial Sequence
<220> FEATURE:
<223> OTHER INFORMATION: Description of Artificial Sequence:human-mouse
      transgenic construct HuZAF VH

```
<400> SEQUENCE: 8

Met Gly Trp Ser Trp Ile Phe Leu Phe Leu Ser Gly Thr Ala Gly
 1               5                  10                  15

Val His Ser Gln Val Gln Leu Val Gln Ser Gly Ala Glu Leu Lys Lys
                 20                  25                  30

Pro Gly Ser Ser Val Lys Val Ser Cys Lys Ala Ser Gly Tyr Ile Phe
            35                  40                  45

Thr Ser Ser Trp Ile Asn Trp Val Lys Gln Ala Pro Gly Gln Gly Leu
        50                  55                  60

Glu Trp Ile Gly Arg Ile Asp Pro Ser Asp Gly Glu Val His Tyr Asn
65                  70                  75                  80

Gln Asp Phe Lys Asp Lys Ala Thr Leu Thr Val Asp Lys Ser Thr Asn
                85                  90                  95

Thr Ala Tyr Met Glu Leu Ser Ser Leu Arg Ser Glu Asp Thr Ala Val
            100                 105                 110

Tyr Tyr Cys Ala Arg Gly Phe Leu Pro Trp Phe Ala Asp Trp Gly Gln
        115                 120                 125

Gly Thr Leu Val Thr Val Ser Ser
        130                 135

<210> SEQ ID NO 9
<211> LENGTH: 114
<212> TYPE: PRT
<213> ORGANISM: Artificial Sequence
<220> FEATURE:
<223> OTHER INFORMATION: Description of Artificial Sequence:humanized
      immunoglobulin huXAF

<400> SEQUENCE: 9

Gln Val Gln Leu Val Gln Ser Gly Ala Glu Leu Lys Lys Pro Gly Ser
 1               5                  10                  15

Ser Val Lys Val Ser Cys Lys Ala Ser Gly Tyr Ile Phe Thr Ser Ser
                 20                  25                  30

Trp Ile Asn Trp Val Arg Gln Ala Pro Gly Gln Gly Leu Glu Trp Ile
            35                  40                  45

Gly Arg Ile Asp Pro Ser Asp Gly Glu Val His Tyr Asn Gln Asp Phe
        50                  55                  60

Lys Asp Lys Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Phe Leu Pro Trp Phe Ala Asp Trp Gly Gln Gly Thr Leu
            100                 105                 110

Val Thr

<210> SEQ ID NO 10
<211> LENGTH: 114
<212> TYPE: PRT
<213> ORGANISM: Artificial Sequence
<220> FEATURE:
<223> OTHER INFORMATION: Description of Artificial Sequence:humanized
      immunoglobulin huZAF

<400> SEQUENCE: 10

Gln Val Gln Leu Val Gln Ser Gly Ala Glu Leu Lys Lys Pro Gly Ser
 1               5                  10                  15

Ser Val Lys Val Ser Cys Lys Ala Ser Gly Tyr Ile Phe Thr Ser Ser
```

-continued

```
                20                  25                  30
Trp Ile Asn Trp Val Lys Gln Ala Pro Gly Gln Gly Leu Glu Trp Ile
            35                  40                  45

Gly Arg Ile Asp Pro Ser Asp Gly Glu Val His Tyr Asn Gln Asp Phe
        50                  55                  60

Lys Asp Lys Ala Thr Leu Thr Val Asp Lys Ser Thr Asn Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Phe Leu Pro Trp Phe Ala Asp Trp Gly Gln Gly Thr Leu
            100                 105                 110

Val Thr

<210> SEQ ID NO 11
<211> LENGTH: 114
<212> TYPE: PRT
<213> ORGANISM: Artificial Sequence
<220> FEATURE:
<223> OTHER INFORMATION: Description of Artificial Sequence:humanized
      immunoglobulin haf25

<400> SEQUENCE: 11

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ile Phe Thr Ser Ser
                20                  25                  30

Trp Ile Asn Trp Val Arg Gln Ala Pro Gly Gln Gly Leu Glu Trp Ile
            35                  40                  45

Gly Arg Ile Asp Pro Ser Asp Gly Glu Val His Tyr Asn Gln Asp Phe
        50                  55                  60

Lys Asp Lys Ala Thr Leu Thr Val Asp Lys Ser Thr Asn Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Phe Leu Pro Trp Phe Ala Asp Trp Gly Gln Gly Thr Leu
            100                 105                 110

Val Thr

<210> SEQ ID NO 12
<211> LENGTH: 107
<212> TYPE: PRT
<213> ORGANISM: Homo sapiens
<220> FEATURE:
<223> OTHER INFORMATION: Variable region of the human Eu antibody light
      chain.

<400> SEQUENCE: 12

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Asn Thr Trp
                20                  25                  30

Leu Ala Trp Tyr Gln Gln Lys Pro Gly Lys Ala Pro Lys Leu Leu Met
            35                  40                  45

Tyr Lys Ala Ser Ser Leu Glu Ser Gly Val Pro Ser Arg Phe Ile Gly
        50                  55                  60

Ser Gly Ser Gly Thr Glu Phe Thr Leu Thr Ile Ser Ser Leu Gln Pro
 65                  70                  75                  80
```

-continued

```
Asp Asp Phe Ala Thr Tyr Tyr Cys Gln Gln Tyr Asn Ser Asp Ser Lys
            85                  90                  95

Met Phe Gly Gln Gly Thr Lys Val Glu Val Lys
            100                 105

<210> SEQ ID NO 13
<211> LENGTH: 117
<212> TYPE: PRT
<213> ORGANISM: Homo sapiens
<220> FEATURE:
<223> OTHER INFORMATION: Variable region of the human Eu antibody heavy
      chain.

<400> SEQUENCE: 13

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Arg Ser
             20                  25                  30

Ala Ile Ile Trp Val Arg Gln Ala Pro Gly Gln Gly Leu Glu Trp Met
         35                  40                  45

Gly Gly Ile Val Pro Met Phe Gly Pro Pro Asn Tyr Ala Gln Lys Phe
     50                  55                  60

Gln Gly Arg Val Thr Ile Thr Ala Asp Glu Ser Thr Asn Thr Ala Tyr
 65                  70                  75                  80

Met Glu Leu Ser Ser Leu Arg Ser Glu Asp Thr Ala Phe Tyr Phe Cys
             85                  90                  95

Ala Gly Gly Tyr Gly Ile Tyr Ser Pro Glu Glu Tyr Asn Gly Gly Leu
            100                 105                 110

Val Thr Val Ser Ser
            115
```

HUMANIZED ANTIBODIES TO γ-INTERFERON

CROSS-REFERENCE TO RELATED APPLICATIONS

This application claims priority from provisional patent application U.S. Ser. No. 60/110,523, filed Dec. 1, 1998, the disclosure of which is incorporated herein by reference.

FIELD OF THE INVENTION

The present invention relates generally to the combination of recombinant DNA and monoclonal antibody technologies for developing novel biologics and, more particularly, for example, to the production of non-immunogenic (in humans) immunoglobulins specific for gamma-interferon (γ-IFN) and their uses in vitro and in vivo. The present invention also relates more specifically to humanized monoclonal antibodies against γ-IFN, polynucleotide sequences encoding the antibodies, a method of producing the antibodies, pharmaceutical compositions comprising the antibodies as an active ingredient, and therapeutic agents for suppressing undesired immune responses comprising the antibodies as an active ingredient.

BACKGROUND

The mammalian immune response is mediated by several types of cells that interact specifically with foreign material, i.e., antigens. One of these cell types, B cells, is responsible for the production of antibodies. Another cell type, T cells, include a wide variety of cellular subsets that destroy cells infected with virus or control the in vivo function of both B cells and other hematopoietic cells, including T cells. A third cell type, macrophages, process and present antigens in conjunction with major histocompatibility complex (MHC) proteins to T cells. Communication between these cell types is mediated in a complex manner by lymphokines, such as interleukins 1–6 and γ-IFN (see, generally, Paul, W. E., ed., *Fundamental Immunology*, 3rd ed., Raven Press, New York (1993), which is incorporated herein in relevant part by reference.)

One important lymphokine is γ-IFN, which is secreted by some T cells. In addition to its anti-viral activity, γ-IFN stimulates natural killer (NK) cells and T helper 1 (Th1) cells, activates macrophages, and stimulates the expression of MHC molecules on the surface of cells (Paul, op. cit., pp. 764–766). Hence γ-IFN generally serves to enhance many aspects of immune function, and is a logical candidate for a therapeutic drug in cases where such enhancement is desired, e.g., in treating cancer. Conversely, in disease states where the immune system is over-active, e.g., autoimmune diseases and organ transplant rejection, antagonists of γ-IFN can be useful to treat the disease by neutralizing the stimulatory effects of γ-IFN.

Mouse monoclonal antibodies that bind to and neutralize γ-IFN have been reported (see, e.g., Van der Meide et al., *J. Gen. Virol*, 67, 1059 (1986)). Such anti-γ-IFN antibodies have been reported to delay or prevent rejection in vitro and in vivo mouse models of transplants, (Landolfo et al., *Science* 229, 176 (1985) and Rosenberg et al., *J. Immunol.* 144, 4648 (1990)), both of which are incorporated herein by reference). Treatment of mice prone to develop a syndrome like systemic lupus erythematosus (SLE) with a monoclonal antibody to γ-IFN was reported to delay onset of the disease (Jacob et al., *J. Exp. Med.* 166, 798 (1987)). An anti-γ-IFN antibody has also been reported to alleviate adjuvant arthritis in rats (Jacob et al., *J. Immunol.* 142, 1500 (1989))and colitis in mice. (Powrie et al., *Immunity* 1, 553–562 (1994)). Queen et al., WO 92/11018 discuss the mouse AF2 antibody to γ-IFN, certain humanized immunoglobulins, and use of the same for treating inflammatory disease.

The use of non-human monoclonal antibodies such as AF2 has certain drawbacks in human treatment, particularly in repeated therapeutic regimens as explained below. Mouse monoclonal antibodies, for example, have a relatively short circulating half-life in humans, and lack other important immunoglobulin functional characteristics when used in humans.

Perhaps more importantly, murine monoclonal antibodies contain substantial amino acid sequences that will be immunogenic when injected into a human patient. Numerous studies have shown that, after injection of a foreign antibody, the immune response elicited by a patient against the injected antibody can be quite strong, essentially eliminating the antibody's therapeutic utility after an initial treatment. Moreover, if mouse or other antigenic (to humans) monoclonal antibodies are used to treat various human diseases, subsequent treatments with unrelated mouse antibodies may be ineffective or even dangerous in themselves, because of cross-reactivity.

Thus, there is a need for improved forms of humanized immunoglobulins specific for γ-IFN antigen that are substantially non-immunogenic in humans, yet easily and economically produced in a manner suitable for therapeutic formulation and other uses. The present invention fulfills these and other needs.

OBJECTS AND SUMMARY OF THE INVENTION

It is the object of the present invention to provide humanized monoclonal antibodies against γ-IFN; polynucleotide sequences encoding the antibodies; a method for producing the antibodies; a pharmaceutical composition comprising the antibodies as an active ingredient; a therapeutic agent for treating diseases, particularly autoimmune diseases, and for immune system suppression comprising the antibody as an active ingredient; and a method for treating such diseases.

The invention provides humanized immunoglobulins that are humanized versions of the mouse AF2 immunoglobulin. The mouse AF2 immunoglobulin is characterized by a light chain variable region designated SEQ ID No:2 and a heavy chain variable region designated SEQ ID No:4. The humanized immunoglobulins of the invention comprise humanized heavy and light chains. Position 11 of the humanized heavy chain variable region framework is occupied by the amino acid present in the equivalent position of the mouse AF2 heavy chain variable region framework. A preferred humanized immunoglobulin of the invention comprises a humanized light chain variable region designated SEQ ID No:6 and a humanized heavy chain variable region designated SEQ ID No:8.

The humanized immunoglobulins specifically bind to the γ-IFN antigen and neutralize γ-IFN. The humanized immunoglobulins are also capable of blocking the binding of the CDR-donating mouse monoclonal antibody to γ-IFN.—IFN. Preferred humanized immunoglobulins have two pairs of light chain/heavy chain complexes, at least one chain comprising one or more mouse complementarity determining regions (CDRs) functionally joined to human framework region segments. For example, mouse CDRs, with or without additional naturally-associated mouse amino acid residues, can be introduced into human framework regions to produce humanized immunoglobulins capable of binding to the antigen at affinity levels stronger than about $10^7$ $M^{-1}$.

The immunoglobulins, including binding fragments and other derivatives thereof, of the present invention can be produced readily by a variety of recombinant DNA techniques, with ultimate expression in transfected cells, preferably immortalized eukaryotic cells, such as myeloma or hybridoma cells. Polynucleotides comprising a first sequence coding for humanized immunoglobulin framework regions and a second sequence coding for the desired immunoglobulin CDRs can be produced synthetically or by combining appropriate cDNA and genomic DNA segments.

The humanized immunoglobulins can be utilized in substantially pure form and can be prepared in a pharmaceutically accepted dosage form, which varies depending on the mode of administration.

BRIEF DESCRIPTION OF THE FIGURES

FIGS. 1A and 1B. Sequences of the cDNA and translated amino acid sequences of the light chain (A) (SEQ ID NOS: 1 and 2) and heavy chain (B) (SEQ ID NOS:3 and 4) variable regions of the mouse antibody AF2. The Kabat CDR sequences are underlined.

FIGS. 2A and 2B: cDNA (SEQ ID Nos. 5 & 7) and amino acid (SEQ ID Nos. 6 & 8) sequences of the mature variable regions of light and heavy chains of humanized antibody HuZAF. Kabat CDRs are underlined.

FIG. 3 Comparison of the heavy chain variable region amino acid sequence humanized immunoglobulin HuZAF SEQ ID NO: 10 and humanized immunoglobulins haf25, SEQ ID NO: 11 and HuXAF SEQ ID NO: 9.

DEFINITIONS

Figure 4:
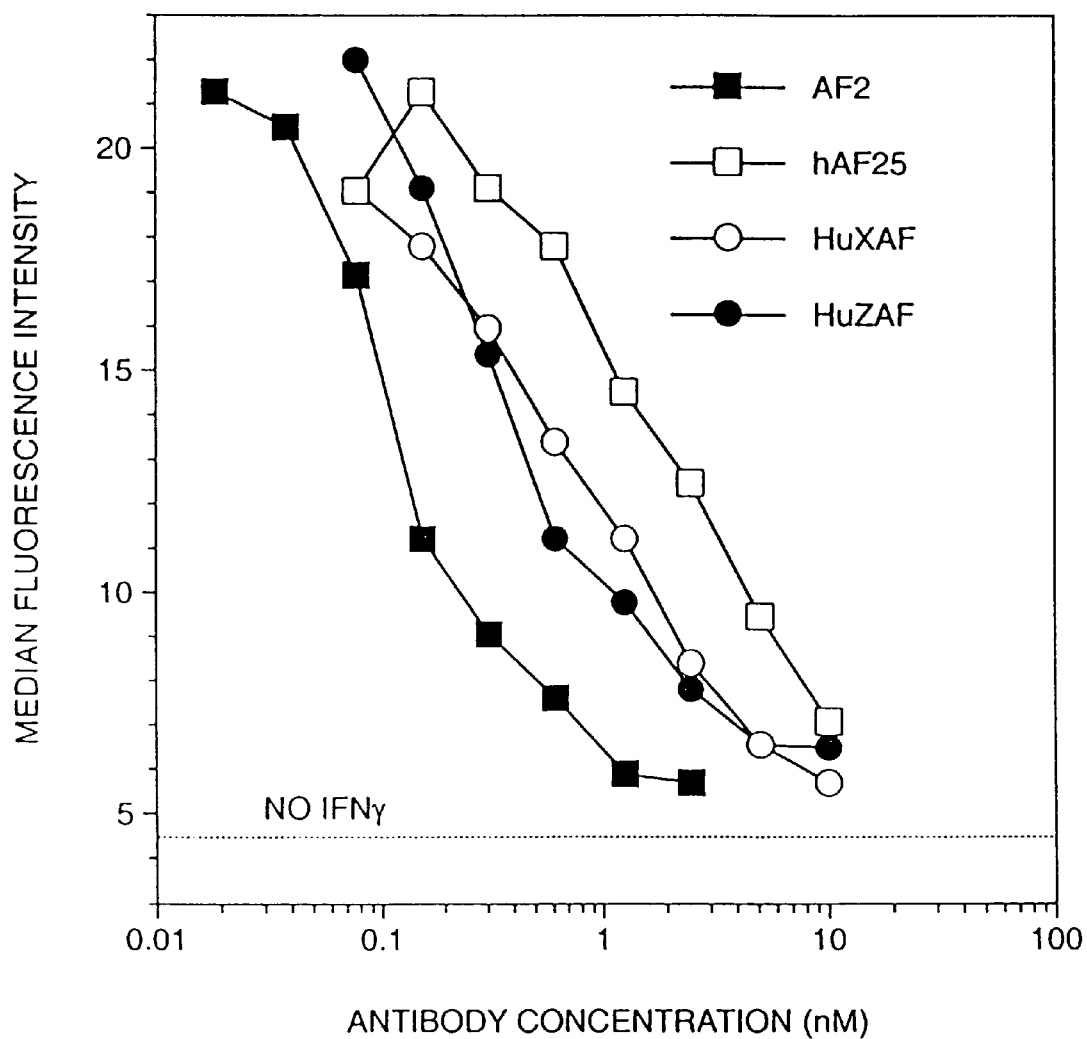
FIG. 4: Neutralization activity of mouse AF2, and humanized antibodies haf25, HuXAF and HuZAF to γ-IFN.

The phrase "substantially identical," in the context of two nucleic acids or polypeptides (e.g., DNAs encoding a humanized immunoglobulin or the amino acid sequence of the humanized immunoglobulin) refers to two or more sequences or subsequences that have at least about 80%, most preferably 90–95% or higher nucleotide or amino acid residue identity, when compared and aligned for maximum correspondence, as measured using the following sequence comparison method and/or by visual inspection. Such "substantially identical" sequences are typically considered to be homologous. Preferably, the "substantial identity" exists over a region of the sequences that is at least about 50 residues in length, more preferably over a region of at least about 100 residues, and most preferably the sequences are substantially identical over at least about 150 residues, or over the full length of the two sequences to be compared. As described below, any two antibody sequences can only be aligned in one way, by using the numbering scheme in Kabat. Therefore, for antibodies, percent identity has a unique and well-defined meaning.

Amino acids from the variable regions of the mature heavy and light chains of immunoglobulins are designated Hx and Lx respectively, where x is a number designating the position of an amino acid according to the scheme of Kabat, *Sequences of Proteins of Immunological Interest* (National Institutes of Health, Bethesda, Md., 1987 and 1991). Kabat lists many amino acid sequences for antibodies for each subgroup, and lists the most commonly occurring amino acid for each residue position in that subgroup to generate a consensus sequence. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat by reference to conserved amino acids. The use of the Kabat numbering system readily identifies amino acids at equivalent positions in different antibodies. For example, an amino acid at the L50 position of a human antibody occupies the equivalent position to an amino acid position L50 of a mouse antibody.

The basic antibody structural unit is known to comprise a tetramer. Each tetramer is composed of two identical pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function. The variable regions of each light/heavy chain pair form the antibody binding site. Thus, an intact antibody has two binding sites.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology*, Paul, W., ed., 3rd ed. Raven Press, N.Y., 1993, SH. 9 (incorporated by reference in its entirety for all purposes)).

From N-terminal to C-terminal, both light and heavy chain variable regions comprise alternating framework and complementarity determining regions (CDRs): FR, CDR. FR, CDR. FR, CDR and FR. The assignment of amino acids to each region is in accordance with the definitions of Kabat (1987) and (1991), supra, and/or Chothia & Lesk, *J. Mol. Biol.* 196:901–917 (1987); Chothia et al., *Nature* 342:878–883 (1989).

Preferably, analogs of exemplified humanized immunoglobulins differ from exemplified immunoglobulins by conservative amino acid substitutions. For purposes of classifying amino acids substitutions as conservative or nonconservative, amino acids may be grouped as follows: Group I (hydrophobic sidechains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

The term epitope includes any protein determinant a capable of specific binding to an immunoglobulin. Epitopic determinants usually consist of chemically active surface groupings of molecules such as amino acids or sugar side chains and usually have specific three dimensional structural characteristics, as well as specific charge characteristics.

As used herein, the term "immunoglobulin" refers to tetrameric antibodies as well as a variety of forms besides antibodies; including, for example, Fv, Fab, and F(ab')$_2$ as well as bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879–5883 (1988) and Bird et al., Science 242, 423–426 (1988), which are incorporated herein by reference). (See, generally, Hood et al., Immunology, Benjamin, N.Y., 2$^{ND}$ ed. (1984), Harlow and Lane, *Antibodies. A Laboratory Manual*, Cold Spring Harbor Laboratory (1988) and Hunkapiller and Hood, Nature, 323, 15–16 (1986), which are incorporated herein by reference.).

As used herein, the term "framework region" refers to those portions of immunoglobulin light and heavy chain variable regions that are relatively conserved (i.e., other than the CDRs) among different immunoglobulins in a single species, as defined by Kabat, et al., op. cit. As used herein, a "human framework region" is a framework region that is substantially identical (about 85% or more) to the framework region of a naturally occurring human antibody.

As used herein, the term "humanized immunoglobulin" refers to an immunoglobulin comprising a human framework, at least one CDR from a non-human antibody, and in which any constant region present is substantially identical to a human immunoglobulin constant region, i.e., at least about 85–90%, preferably at least 95% identical. Hence, all parts of a humanized immunoglobulin, except possibly the CDRs, are substantially identical to corresponding parts of one or more native human immunoglobulin sequences. For example, a humanized immunoglobulin would not encompass a chimeric mouse variable region/human constant region antibody.

The term "patient" includes human and veterinary subjects.

The term "substantially pure" or "isolated" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition comprises more than about 80, 90, 95 or 99% percent by weight of all macromolecular species present in the composition. Most preferably, the object species is purified to essential homogeneity (contaminant species cannot be detected in the composition by conventional detection methods) wherein the composition consists essentially of a single macromolecular species.

DETAILED DESCRIPTION

The invention provides humanized immunoglobulins that specifically bind to γ-IFN, and methods of using the same for suppressing undesired immune responses.

I. Humanized Antibodies Specific for γ-IFN

Humanized immunoglobulins of the invention have variable framework regions substantially from a human immunoglobulin (termed an acceptor immunoglobulin), preferably the human acceptor antibody EU, and CDRs substantially from a mouse immunoglobulin termed AF2 (referred to as the donor immunoglobulin). The constant region(s), if present, are also substantially from a human immunoglobulin. The humanized antibodies exhibit a specific binding affinity for γ-IFN of at least $10^7$, $10^8$, $10^9$, or $10^{10}$ $M^{-1}$. Usually the upper limit of binding affinity of the humanized antibodies for human γ-IFN is within a factor of 3, 4, 5 or 10 of that of AF2. Often the lower limit of binding affinity is also within a factor of 3, 4, 5 or 10 of that of AF2. Preferred humanized immunoglobulins compete with AF2 for binding to γ-IFN and prevent γ-IFN from binding to and thereby transducing a response through a γ-IFN receptor. The humanized antibodies preferably neutralize 80,90, 95 or 99% of γ-interferon activity at 1, 2, 5, 10, 20, 50 or 100-fold molar excess.

The mouse AF2 antibody is described by Queen et al., WO 92/11018, and has heavy and light chain variable regions designated SEQ ID Nos: 2 and 4. The mouse antibody has IgG2b isotype and a kappa light chain. The heavy and light chain variable regions of the preferred human acceptor antibody EU, and those of other possible human acceptor antibody are described by Kabat, *Sequences of Proteins of Immunological Interest* (National Institutes of Health, Bethesda, Md., 1987 and 1991). The human acceptor antibody is chosen such that its variable regions exhibit a high degree of sequence identity with those of the mouse AF2 antibody. The heavy and light chain variable framework regions can be derived from the same or different human antibody sequences. The human antibody sequences can be the sequences of naturally occurring human antibodies or can be consensus sequences of several human antibodies.

The design of humanized immunoglobulins can be carried out as follows. When an amino acid falls under the following category, the framework amino acid of a human immunoglobulin to be used (acceptor immunoglobulin) is replaced by a framework amino acid from a CDR-providing non-human immunoglobulin (donor immunoglobulin):

(a) the amino acid in the human framework region of the acceptor immunoglobulin is unusual for human immunoglobulins at that position, whereas the corresponding amino acid in the donor immunoglobulin is typical for human immunoglobulins in that position;

(b) the position of the amino acid is immediately adjacent to one of the CDRs; or (c) the amino acid is capable of interacting with the CDRs (see, Queen et al., op. cit., and Co et al., Proc. Natl. Acad. Sci. USA 88, 2869 (1991), respectively, both of which are incorporated herein by reference). For a detailed description of the production of humanized immunoglobulins see, Queen et al., op. cit., and Co et al., op. cit.

Queen et al., WO 92/11018 report certain humanized forms of AF2, comprising CDR regions from AF2 and variable region frameworks from EU in which certain positions are substituted. The present humanized immunoglobulins preferably contain the same substitutions as described by Queen et al., supra. However, additional substitutions are also present. Specifically, position H11 is substituted with the amino acid occupying the equivalent position of the mouse AF2 heavy chain.

Position H11 does not fulfill the criteria for substitution given above, but nevertheless makes a significant contribution to neutralizing activity in humanized immunoglobulins incorporating this substitution. The desirability of substituting at this position was determined by substitution of various positions in a chimeric AF2 antibody (i.e., having mouse variable domains and human constant regions) with amino acids from equivalent positions in the human EU antibody (SEQ ID NOS:12 and 13). Substitution of position H11 caused a significant reduction in the neutralizing activity of the chimeric antibody for γ-IFN.

Usually the CDR regions in humanized antibodies are substantially identical, and more usually, identical to the corresponding CDR regions in the mouse antibody from which they were derived. Although not usually desirable, it is sometimes possible to make one or more conservative amino acid substitutions of CDR residues without appreciably affecting the binding affinity of the resulting humanized immunoglobulin. Occasionally, substitutions of CDR regions can enhance binding affinity.

Other than for the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin.

Analogs of HuZAF show substantial amino acid sequence identity with HuZAF. Heavy and light chain variable regions of analogs are encoded by nucleic acid sequences that hybridize with the nucleic acids encoding the heavy or light chain variable regions of HuZAF, or degenerate forms thereof, under stringent conditions. Phage-display technology offers powerful techniques for selecting such analogs of HuZAF with retaining binding affinity and specificity (see, e.g., Dower et al., WO 91/17271; McCafferty et al., WO 92/01047; and Huse, WO 92/06204 (each of which is incorporated by reference in its entirety for all purposes).

The variable segments of humanized antibodies produced as described supra are typically linked to at least a portion of an immunoglobulin constant region (Fc), typically that of a human immunoglobulin. Human constant region DNA sequences can be isolated in accordance with well-known procedures from a variety of human cells, but preferably immortalized B-cells (see Kabat et al., supra, and WO87/02671). Ordinarily, the antibody contains both light chain and heavy chain constant regions. The heavy chain constant region usually includes CH1, hinge, CH2, CH3, and, sometimes, CH4 regions.

The humanized antibodies include antibodies having all types of constant regions, including IgM, IgG, IgD, IgA and IgE, and any isotype, including IgG1, IgG2, IgG3 and IgG4. When it is desired that the humanized antibody exhibit cytotoxic activity, the constant domain is usually a complement-fixing constant domain and the class is typically $IgG_1$. When such cytotoxic activity is not desirable, the constant domain can be of the $IgG_2$ class. The humanized antibody may comprise sequences from more than one class or isotype.

Having conceptually selected the CDR and framework components of humanized immunoglobulins, a variety of methods are available for producing such immunoglobulins. Because of the degeneracy of the genetic code, a variety of nucleic acid sequences encode each immunoglobulin amino acid sequence. The desired nucleic acid sequences can be produced by de novo solid-phase DNA synthesis or by PCR mutagenesis of an earlier prepared variant of the desired polynucleotide. All nucleic acids encoding the antibodies described in this application are expressly included in the invention.

Once expressed, the whole antibodies, their dimers, individual light and heavy chains, or other immunoglobulin forms of the present invention can be purified according to standard procedures in the art, including ammonium sulfate precipitation, affinity columns, column chromatography, gel electrophoresis and the like (see, generally, Scopes, R., *Protein Purification*, Springer-Verlag, N.Y. (1982), which is incorporated herein by reference). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically (including extracorporeally) or in developing and performing assay procedures, immunofluorescent stainings, and the like. (See, generally, *Immunological Methods*, Vols. I and II, Lefkovits and Pernis, eds., Academic Press, New York, N.Y. (1979 and 1981).

II. Therapeutic Methods

Pharmaceutical compositions comprising immunoglobulins of the present invention are useful for parenteral administration, i.e., subcutaneously, intramuscularly and particularly, intravenously. The compositions for parenteral administration commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, histidine and arginine. The concentration of the immunoglobulins in these formulations can vary widely, i.e., from less than about 0.01%, usually at least about 0.1% to as much as 5% by weight and are selected primarily based on fluid volumes, and solubilities in accordance with the particular mode of administration selected.

Thus, a typical pharmaceutical composition for injection could be made up to contain 1 ml sterile buffered water, and 1–100 mg of immunoglobulin. A typical composition for intravenous infusion can be made up to contain 250 ml of sterile Ringer's solution, and 10 mg of immunoglobulin. Actual methods for preparing parentally administerable compositions are known or apparent to those skilled in the art and are described in more detail in, for example, Remington's *Pharmaceutical Science* (15th Ed., Mack Publishing Company, Easton, Pa., 1980), which is incorporated herein by reference.

The immunoglobulins of this invention can be frozen or lyophilized for storage and reconstituted in a suitable carrier prior to use. This technique has been shown to be effective with conventional immunoglobulins and art-known lyophilization and reconstitution techniques can be employed. Lyophilization and reconstitution can lead to varying degrees of immunoglobulin activity loss (e.g., with conventional immunoglobulins, IgM antibodies tend to have greater activity loss than IgG antibodies) and that use levels may have to be adjusted to compensate.

The compositions can be administered for prophylactic and/or therapeutic treatments. In therapeutic application, compositions are administered to a patient already suffering from an undesired immune response in an amount sufficient to cure or at least partially arrest the condition and its complications. An amount adequate to accomplish this is defined as a "therapeutically effective dose." Amounts effective for this use depend upon the severity of the condition and the general state of the patient's own immune system, but generally range from about 0.01 to about 100 mg of antibody per dose, with dosages of from 0.1 to 50 mg and 1 to 10 mg per patient being more commonly used. Single or multiple administrations on a daily, weekly or monthly schedule can be carried out with dose levels and pattern being selected by the treating physician. It must be kept in mind that the materials of this invention may generally be employed in serious disease states, that is life-threatening or potentially life-threatening situations. In such cases, in view of the minimization of extraneous substances and the lower probability of "foreign substance" rejections which are achieved by the present humanized immunoglobulins of this invention, it is possible and may be felt desirable by the treating physician to administer substantial excesses of these immunoglobulins.

In prophylactic applications, compositions are administered to a patient who is at risk of developing an inappropriate immune response in an amount sufficient to suppress the response. Such an amount is defined to be a "prophylactically effective dose." In this use, the precise amounts again depend upon the patient's state of health and general level of immunity, but generally range from 0.1 to 100 mg per dose, especially 1 to 10 mg per patient.

The methods are effective on a variety of disease states associated with undesired immune response mediated by HLA class II antigens and/or Th1 cells. Such disease states include graft versus host disease and transplant rejection in patients undergoing an organ transplant, such as heart, lung, kidney, and liver, and autoimmune diseases, such as Type I diabetes, multiple sclerosis, rheumatoid arthritis, systemic lupus erythematosus, Hashimoto's thyroiditis, psoriasis primary biliary cirrhosis, and inflammatory bowel disease, e.g., Crohn's disease.

The humanized immunoglobulins can be utilized alone in substantially pure form, or together with a chemotherapeutic agent such as a non-steroidal anti-inflammatory drug, a corticosteroid, or an immunosuppressant. The agents can include non-steroidal anti-inflammatory agents (e.g., aspirin, ibuprofen), steroids (e.g., prednisone) and immunosuppressants (e.g., cyclosporin A, methotrexate cytoxan)

Humanized immunoglobulins of the present invention can also be used in combination with other antibodies, particularly humanized antibodies reactive with other lymphokines or lymphokine receptors. For example, suitable antigens to which a cocktail of humanized immunoglobulins may react include interleukins 1 through 18 and the p55 and p75 chains of the IL-2 receptor (see, Waldmann, *Annu. Rev. Biochem.* 58, 875 (1989) and Queen et al., *Proc. Natl. Acad. Sci. USA* 86, 10029 (1989), both of which are incorporated herein by reference). Other antigens include those on cells responsible for the disease, e.g., the so-called "Clusters of Differentiation" (Leucocyte Typing III, ed. by A. J. McMichael, Oxford University Press 1987), which is incorporated herein by reference).

Diagnostic Methods

Humanized anti-γ-IFN antibody is also useful in diagnostic methods. Humanized anti-γ-IFN antibody is useful for measuring expression of γ-IFN, and consequent development of an immune response. Methods of diagnosis can be performed in vitro using a cellular sample (e.g., blood sample, lymph node biopsy or tissue) from a patient or can be performed by in vivo imaging. Humanized anti-γ-IFN antibody is also useful for purifying human γ-IFN.

In particular embodiments, compositions comprising humanized immunoglobulin of the present invention can be used to detect γ-IFN, for example, by radioimmunoassay or ELISA. Thus, a humanized immunoglobulin of the present invention, such as a humanized immunoglobulin that binds to the antigen determinant identified by the AF2 antibody can be labeled and used to identify anatomic sites that contain significant concentrations of γ-IFN. For example but not for limitation, one or more labeling moieties can be attached to the humanized immunoglobulin. Exemplary labeling moieties include, but are not limited to, radiopaque dyes, radiocontrast agents, fluorescent molecules, spin-labeled molecules, enzymes, or other labeling moieties of diagnostic value, particularly in radiologic or magnetic resonance imaging techniques.

The following examples are offered by way of illustration, not by limitation. It will be understood that although the examples pertain to the humanized AF2 antibody, producing humanized antibodies with high binding affinity for the γ-IFN antigen it is also contemplated using CDRs from other monoclonal antibodies that bind to an epitope of γ-IFN.

All publications mentioned herein are incorporated herein by reference for the purpose of describing and disclosing, for example, the constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

EXAMPLES

1. Production of Humanized Immunoglobulins
Cloning and Sequencing of Mouse AF2 Variable Region cDNAs Cloning of cDNA sequences encoding the variable regions of the light and heavy chains of the mouse AF2 antibody is described by Queen et al., WO 92/11018. The sequences of these cDNAs are shown in FIG. 1.

Two plasmid vectors were prepared for construction and expression of a chimeric antibody comprising the variable domains of the mouse AF2 antibody linked to human constant regions. The plasmid pVg1-dhfr (Queen et al., supra contains a human cytomegalovirus IE1 promoter and enhancer (M. Boshart et al., Cell 41, 521 (1985)), the human genomic Cg1 segment including part of the preceding intron, and a dihydrofolate reductase (dhfr) gene (Simonsen et al., Proc. Natl. Acad. Sci. USA 80, 2495 (1984), which is incorporated herein by reference) for selection. The plasmid pVk (Queen et al., supra) is similar to pVg1-dhfr but contains the human genomic Ck segment and the gpt gene. Derivatives of the AF2 heavy and light chain variable regions were prepared from the cDNAs by polymerase chain reaction. The 5' primers hybridized to the V regions starting at the ATG codons and contained XbaI sites; the 3' primers hybridized to the last 15 nucleotides of the J regions and contained splice donor signals and XbaI sites (see, Queen et al., *Proc. Natl. Acad. Sci. USA* 86, 10029 (1989), which is incorporated herein by reference). The modified V regions were cloned into the XbaI sites of the respective plasmid vectors between the CMV promoter and the partial introns of the constant regions.

For expression of the chimeric antibody, the heavy chain and kappa chain plasmids were transfected into Sp2/0 mouse myeloma cells by electroporation and cells selected for gpt expression. Clones secreting a maximal amount of complete antibody were detected by ELISA. Chimeric AF2 antibody was shown to bind to human γ-IFN by ELISA.

Design of Humanized AF2 Variable Regions

To retain the binding affinity of the mouse antibody in the humanized antibody, the general procedures of Queen et al.

were followed (Queen et al. *Proc. Natl. Acad. Sci. USA* 86: 10029 (1989) and U.S. Pat. Nos. 5,585,089 and 5,693,762). The choice of framework residues can be critical in retaining high binding affinity In principle, a framework sequence from any human antibody can serve as the template for CDR grafting; however, it has been demonstrated that straight CDR replacement into such a framework can lead to significant loss of binding affinity to the antigen (Tempest et al., *Biotechnology* 9: 266 (1992); Shalaby et al., *J. Exp. Med.* 17: 217 (1992)). The more homologous a human antibody is to the original murine antibody, the less likely will the human framework introduce distortions into the mouse CDRs that could reduce affinity. Based on a sequence homology search against an antibody sequence database, the human antibody Eu was chosen as providing good framework homology to the mouse AF2 antibody. Other highly homologous human antibody chains would also be suitable to provide the humanized antibody framework, especially kappa light chains from human subgroup I and heavy chains from human subgroup I (as defined by Kabat et al., *Sequences of Proteins of Immunological Interest*, 5th ed., U.S. Department of Health and Human Services, 1991).

The computer programs ABMOD and ENCAD (Levitt et al., *J. Mol. Biol.* 168: 595 (1983)) were used to construct a molecular model of the AF2 variable domain, which was used to locate the amino acids in the AF2 framework that are close enough to the CDRs to potentially interact with them. To design the humanized HuZAF heavy and light chain variable regions, the CDRs from the mouse AF2 antibody were grafted into the framework regions of the human Eu antibody. At framework positions where the computer model suggested significant contact with the CDRs, the amino acids from the mouse antibody were substituted for the original human framework amino acids. For the humanized form of AP2 designated HuZAF, this was done at residues 27, 28 (within Chothia CHR H1), 30, 38, 48, 67, 68, 70, 72, 74, 98 and 107 of the heavy chain and at residues 48, 63, and 70 of the light chain. Furthermore, framework residues that occurred only rarely at their positions in the database of human antibodies were replaced by a human consensus amino acid at those positions or by the corresponding mouse antibody amino acids. For HuZAF this was done at residues 93, 95, 98, 107, 108, 109, and 111 of the heavy chain and at residue 48, 63 and 70 of the light chain.

In addition, in HuZAF,position H11 was substituted with the amino acid occupying the equivalent position of the heavy chain of mouse antibody AF2. H11 was identified as being a candidate for substitution by substitution of various positions in a chimeric AF2 antibody (i.e., having mouse variable domains except at substituted positions) with amino acids from equivalent positions in the human EU antibody and testing each variant for reduced neutralizing activity. The final sequences of the HuZAF light and heavy chain variable domains incorporating all of the above substitutions are shown in FIGS. 2A and 2B.

Other humanized immunoglobulins were designed also containing mouse AF2 CDR regions and human EU variable regions but containing various subsets of the above substitutions (see FIG. 3). Haf25 is the same as HuZAF except that the antibody lacks substitutions at positions H11 and H38. HuXAF is the same as huZAF except that the former antibody lacks a substitution at position H38.

However, there are many potential CDR-contact residues that are also amenable to substitution and that may still allow the antibody to retain substantial affinity to the antigen. For example, the first four N-terminal amino acid residues in the humanized AF2 light chain can alternatively be substituted with the sequence from the murine antibody because of its contacts with the CDRs.

Likewise, many of the framework residues not in contact with the CDRs in the humanized anti γ-IFN heavy and light chains can accommodate substitutions of amino acids from the corresponding positions of the human EU antibody, from other human antibodies, from the mouse AF2 antibody, or from other mouse antibodies, without significant loss of the affinity or non-immunogenicity of the humanized antibody.

Various alternative amino acids can be selected to produce versions of humanized anti-γ-IFN that have varying combinations of affinity, specificity, non-immunogenicity, ease of manufacture, and other desirable properties. Thus, the examples are offered by way of illustration, not of limitation.

For the construction of genes for the humanized antibodies, nucleotide sequences were selected that encode the protein sequences of the humanized heavy and light chains, plus typical immunoglobulin signal sequences, generally utilizing codons found in the mouse sequence. Several degenerate codons were changed to create restriction sites or to remove undesirable ones. The nucleotide sequences also included the same splice donor signals used in the chimeric genes and an XbaI site at each end. Certain genes were constructed from four overlapping synthetic oligonucleotides. For each variable domain gene, two pairs of overlapping oligonucleotides on alternating strands were synthesized that encompassed the entire coding sequences as well as the signal peptide and the splice donor signal. The oligonucleotides were synthesized on an Applied Biosystems 380B DNA synthesizer. Each oligo was about 110–140 bases long with about a 15 base overlap. Double stranded DNA fragments were synthesized with Klenow polymerase from each pair of oligonucleotides, digested with restriction enzymes, ligated to the pUC18 vector and sequenced. Two fragments with the respectively correct half-sequences were then ligated into the XbaI sites of the pvg1-dhfr or pVk expression vectors in the appropriate orientations to produce the complete heavy and light chain genes. Certain of the genes for the humanized AF2 variants were generated by PCR mutagenesis of previous genes.

The heavy chain and light chain plasmids were transfected into Sp2/0 mouse myeloma cells by electroporation and cells selected for gpt expression. Clones were screened by assaying human antibody production in the culture supernatant by ELISA, and antibody was purified from the best-producing clones. Antibody was purified by passing tissue culture supernatant over a column of staphylococcal protein A-Sepharose CL-4B (Pharmacia). The bound antibody was eluted with 0.2 M. Glycine-HCl, pH 3.0 and neutralized with 1 M Tris pH 8.0. The buffer was exchanged into PBS by passing over a PD10 column (Pharmacia) or by dialysis.

2. Assay for Neutralizing Activity Against γ-IFN

γ-IFN increases the level of expression of MHC molecules on responsive cell lines. Hs294T is a human melanoma cell line that upregulates the amount of MHC class II molecules expressed on the surface when incubated with γ-IFN for 48–72 hr. (Zarniecki et al., J. Immunology, 140, 4217–4223 (1988)). This enhancement can be detected using a monoclonal antibody specific for the upregulated molecule and indirect immunofluorescence and subsequent flow cytometry. An antibody can be assayed for γ-IFN neutralizing activity by measuring whether the antibody inhibits the upregulation of MHC class II molecules on this cell line. γ-IFN for use in the assay was purchased from R&D Systems, 614 McKinley Place, N.E., Minneapolis, Minn. 55413.

Increasing concentrations of antibody were added to a fixed amount of γ-IFN that had previously been shown to upregulate the level of MHC class II molecules on HS294T cells. The cells were incubated for 48–72 hr with the antibody-γ-IFN mixture and examined for the level of MHC class II molecules by indirect immunofluorescence using a mouse monoclonal antibody specific for human MHC class II molecules. Analysis by flow cytometry allowed for the determination of the median fluorescence intensity of the cell population, which was then plotted against antibody concentration to show the neutralizing capacity of the antibody.

As seen in FIG. 4, HuZAF has significantly better neutralizing activity than haf25, i.e., substitutions at positions H11 and H38 improved neutralizing activity. HuXAF also had better neutralizing activity than haf25, indicating that substitutions at H11 alone made an important contribution to neutralizing activity.

What is claimed is:

1. A humanized immunoglobulin, which is a humanized version of the mouse AF2 immunoglobulin having a light chain variable region designated SEQ ID No:2 and a heavy chain variable region designated SEQ ID No:4, the humanized immunoglobulin comprising humanized heavy and light chains, provided that position 11 according to the Kabat numbering system of the humanized heavy chain variable region framework is occupied by the amino acid present in the equivalent position of the mouse AF2 heavy chain variable region framework, wherein the humanized immunoglobulin specifically binds to human γ-IFN with an affinity constant within four-fold of the affinity of the mouse AF2 antibody.

2. The humanized immunoglobulin of claim 1, comprising CDRs from the mouse AF2 immunoglobulin and heavy and light chain variable region frameworks from the human EU immunoglobulin (SEQ ID NOS: 13 and 12.

3. The humanized immunoglobulin of claim 2, further provided that position H38 according to the Kabat numbering system is occupied by the amino acid present in the equivalent position of the mouse AF2 heavy chain variable region framework.

4. The humanized immunoglobulin of claim 2, further provided that position H11, H27, H28, H30, H38, H48, H67, H68, H70, H72, H74, H93, H95, H98, H107, H108, H109, H111 according to the Kabat numbering system are occupied by the amino acid present in the equivalent position of the mouse AF2 heavy chain, positions L48, and L70 according to the Kabat numbering system are occupied by the amino acid present in the equivalent position of the mouse AF2 light chain, and position L63 is occupied by the amino acid present in the equivalent position of a consensus sequence of light chains of human immunoglobulins.

5. The humanized immunoglobulin according to claim 1 that comprises two light chain/heavy chain dimers.

6. The humanized immunoglobulin of claim 1 that is of IgG1 isotype.

7. The humanized immunoglobulin according to claim 1, which is purified to at least 95% homogeneity.

8. A humanized immunoglobulin comprising a mature heavy chain variable region designated SEQ ID No:6 and a mature light chain variable region designated SEQ ID No:8.

* * * * *